United States Patent [19]

von Malsen-Ponickau

[11] Patent Number: 4,748,020

[45] Date of Patent: May 31, 1988

[54] VACCINE FOR DISEASES OF STAPHYLOCOCCUS AUREUS AND METHODS OF PREPARATION

[76] Inventor: Egbert F. von Malsen-Ponickau, P.O. Box/Apartado 428, Puerto de la Cruz Teneriffa, Spain

[21] Appl. No.: 768,116

[22] PCT Filed: Dec. 19, 1984

[86] PCT No.: PCT/EP84/00414

§ 371 Date: Aug. 12, 1985

§ 102(e) Date: Aug. 12, 1985

[87] PCT Pub. No.: WO85/02771

PCT Pub. Date: Jul. 4, 1985

[30] Foreign Application Priority Data

Dec. 19, 1983 [DE] Fed. Rep. of Germany ....... 3345864

[51] Int. Cl.[4] .................. A61K 39/083; C12N 1/38; C12N 1/20

[52] U.S. Cl. .................................... 424/92; 424/88; 424/89; 424/90; 424/93; 435/243; 435/244; 435/245; 435/253; 435/822; 435/883

[58] Field of Search ..................... 424/88–93; 435/243–245, 253, 822, 883

[56] References Cited

U.S. PATENT DOCUMENTS

| | | | |
|---|---|---|---|
| 3,625,833 | 12/1971 | Schaffer | 435/883 |
| 4,197,290 | 4/1980 | Yoshida | 424/92 |
| 4,285,936 | 8/1981 | Pier et al. | 424/92 |
| 4,413,057 | 11/1983 | Carlo et al. | 424/92 |
| 4,472,378 | 9/1984 | Shuster et al. | 424/92 |

*Primary Examiner*—John Kight
*Assistant Examiner*—Garnette D. Draper
*Attorney, Agent, or Firm*—Bierman and Muserlian

[57] ABSTRACT

A vaccine for humans or warm-blooded animals for preventing or curing diseases caused by pathogenic germs, for example Staphylococcus or other bacteria, is obtained by growing the respective pathogenic germ in a form that lives on animal protein alien to warm-blooded animals, for example on fish protein, and incorporating this form of pathogenic germ in the vaccine.

7 Claims, No Drawings

VACCINE FOR DISEASES OF STAPHYLOCOCCUS AUREUS AND METHODS OF PREPARATION

The invention relates to a vaccine against illness and diseases caused in humans or warm-blooded animals by pathogenic agents.

The problem underlying the invention is to provide for all or in any case a number of important diseases in man or warm-blooded animals produced by pathogenic agents, such as viruses, bacteria and fungi, in each case a disease-specific vaccine which effects a permanent or at least temporary immunization against said disease and/or cure of a disease which has already appeared.

The invention is based on the surprising recognition that it is possible to produce selectively forms of pathogenic agents which have lost their pathogenic properties for man or warm-blooded animals but can nevertheless have in man or animals immunization and/or healing effects.

The vaccine according to the invention is characterized in that it contains forms of the respective agents capable of living on protein not from warm-blooded animals. Advantageously these are staphylococci, in particular *Staphylococcus aureus*. However, other forms of bacteria can be used which are capable of living on fish protein, in particular streptococci, pneumococci, *Pseudomonas aeruginosa*, corynebacteria, as well as Salmonella and other pathogens. Apart from fish protein, protein can be used from crustacea, reptiles, amphibia as well as insects and worms.

The invention also relates to a method of growing forms which are non-pathogenic for man and warm-blooded animals. The method is characterized in that pathogenic agents are inoculated into a culture medium with nondenaturated protein of non-warm-blooded animals, in particular fish protein, and a colony grown under the usual cultivation conditions, this operation possibly being repeated. Presumably when this is done an adaptation takes place due to mutation and this produces the aforementioned properties of the finished vaccine.

Advantageously, at the same time mutation or selection-promoting external influences are exerted, in particular irradiation with short-wave electromagnetic radiation, cobalt radiation and/or gamma radiation. Ultraviolet radiation has proved particularly suitable. An important feature of the invention is that pathogenic microorganisms can be combatted.

The invention will be explained below with the aid of examples.

EXAMPLE 1

A *Staphyloccous aureus* was inoculated over a wide area in a Petri dish with the usual nutrient agar and incubated in an incubator at 37° C.

After adequate growth some of the bacteria were transferred by inoculation with a platinum needle in a nutrient medium in a second Petri dish. This Petri dish was also incubated at 37° C. in an incubator and in addition subjected to radiation of an UV lamp.

It was observed that the greater part of the bacteria were not capable of living on the culture medium consisting of fish protein. Only a few of the inoculated bacteria survived.

After adequate reproduction by means of a platinum needle part of the bacteria was again transferred by inoculation to a third culture medium. This was subjected after incubation to UV radiation.

This operation was repeated using new culture mediums each time.

In the present example over 150 culture transfers were necessary but this does not mean that the number could be greater or less with reduplication.

A live vaccine was made directly from the bacteria surviving on the last culture medium. Test animals (mice, rats, guinea pigs, rabbits) were inoculated with this vaccine in amounts corresponding to many times the lethal dose of the original strain. None of the inoculated animals died or showed any signs of disease. Afterwards the inoculated animals as well as uninoculated animals for check purposes were infected with a corresponding virulent strain. Even with injection amounts corresponding to many times the lethal dose for uninoculated animals the inoculated animals proved completely immune. It was possible to check the degree of immunity in the case of rabbits by precipitation according to Ouchterlony.

EXAMPLE 2

In a Petri dish with an agar culture medium as in example 1 a colony of a staphylococci strain was grown. As in example 1, growth was obtained by transfer inoculations to further culture mediums with fish protein. To promote mutation irradiation with long-wave X-ray radiation was applied. A live vaccine was made from the strain thus treated.

Tests according to examples 1 and 2 were carried out with streptococci, in particular *Streptococcus haemolyticus*, as well as *Pseudomonas aeruginosa* and corynebacterium diphtheriae and the results were the same. Furthermore, fresh, i.e. not denaturated protein, was used from other fish, in particular just killed or fresh frozen fish. The protein may be in the form of suspensions, solutions or dispersions. When the cultivation conditions and strength of the radiation are suitably adapted it should be possible to make corresponding non-pathogenic mutation forms of all hitherto known pathogenic bacteria, or of any discovered in furture, as well as of viruses, fungi and mycroplasms. A particularly important point is that warm-blooded animals which already have such a disease can be therapeutically treated.

I claim:

1. A vaccine for diseases caused by Staphylococci aureus in humans and warm-blooded animals containing in a carrier an effective amount of live organisms prepared by (a) growing Staphylococci aureus which cause the disease against which the vaccine is intended to be effective; (b) inocculating the said organisms on a culture medium of protein of non-warm-blooded animals and culturing on this medium until a colony capable of living on this medium until a colony capable of living on this medium is obtained and (c) incorporating live organisms from this colony into the vaccine.

2. A vaccine of claim 1 wherein the organisms are bacteria forms capable of living on fish protein.

3. A method of producing a vaccine for diseases caused by pathogenic agents comprising (a) growing Staphylococci aureus which cause the disease against which the vaccine is intended to be effective; (b) inocculating the said organisms on a culture medium of protein of non-warm blooded animals and culturing on this medium until a colony capable of living on this medium is obtained and (c) incorporating live organisms from this colony into the vaccine.

4. The method of claim 3 wherein the protein is fish protein.

5. The method of claim 3 wherein the culturing step is repeated.

6. The method of claim 3 wherein the culture is subjected to irradiation to exert mutation influences.

7. The method of claim 6 wherein the irradiation is effected with short-wave electromagnetic radiation.

* * * * *